(12) United States Patent
Su et al.

(10) Patent No.: US 10,039,870 B2
(45) Date of Patent: *Aug. 7, 2018

(54) BONE MARROW ASPIRATING PROBE (71) Applicant: Brian W. Su, Kentfield, CA (US)

(72) Inventors: Brian W. Su, Kentfield, CA (US);
Robert Jay Jones, Cedar Park, TX (US)

(73) Assignee: Brian W. Su, Kentfield, CA (US)

( * ) Notice: Subject to any disclaimer, the term of this patent is extended or adjusted under 35 U.S.C. 154(b) by 407 days.

This patent is subject to a terminal disclaimer.

(21) Appl. No.: 14/574,032

(22) Filed: Dec. 17, 2014

(65) Prior Publication Data
US 2015/0165099 A1 Jun. 18, 2015

Related U.S. Application Data (60) Provisional application No. 61/916,804, filed on Dec. 17, 2013.

(51) Int. Cl.
A61M 1/00 (2006.01)

(52) U.S. Cl.
CPC ..... *A61M 1/008* (2013.01); *A61M 2202/0014* (2013.01); *A61M 2202/10* (2013.01)

(58) Field of Classification Search
CPC .......... A61M 1/008; A61M 2202/0024; A61M 2202/10; A61B 10/025; A61B 10/0283
See application file for complete search history.

(56) References Cited

U.S. PATENT DOCUMENTS

| 2007/0066987 A1* | 3/2007 | Scanlan, Jr. ......... | A61B 10/025 606/184 |
| 2007/0179459 A1* | 8/2007 | Geisler ................ | A61B 10/025 604/317 |
| 2008/0119759 A1* | 5/2008 | McLain ............... | A61B 10/025 600/567 |
| 2011/0112436 A1* | 5/2011 | Jones ................... | A61B 10/025 600/567 |
| 2012/0035501 A1* | 2/2012 | Landrigan ............ | A61B 10/025 600/567 |
| 2012/0041395 A1* | 2/2012 | Sweeney ............ | A61B 17/7061 604/272 |
| 2015/0165098 A1* | 6/2015 | Su ........................ | A61M 1/008 604/319 |

* cited by examiner

*Primary Examiner* — Benjamin Klein
(74) *Attorney, Agent, or Firm* — G+J Law Group PLLC; Georgios A. Georgakis (57) ABSTRACT Methods and systems include an aspiration probe that includes a flutes section. The flutes section includes one or more longitudinal channels and another section that is coupled to the flutes section. The other section includes one or more openings corresponding to the one or more longitudinal channels. The flutes are configured to be placed within bone marrow through a hole in a bone. The openings are configured to be coupled to a suction device for generating suction. The flutes are configured to channel the bone marrow from within the bone into the openings based at least upon generating the suction.

10 Claims, 7 Drawing Sheets

BONE MARROW ASPIRATING PROBE

A. PRIORITY CLAIM/INCORPORATION BY REFERENCE

This application claims the benefit of U.S. Provisional Application No. 61/916,804, filed Dec. 17, 2013, entitled "Bone Marrow Aspirating Probe," and naming Brian W. Su et al. as inventors. The above-referenced provisional patent application is hereby incorporated by reference herein in its entirety.

The subject matter of the present application is related to the subject matter of the following commonly assigned, co-pending application, U.S. application Ser. No. 14/574,004, filed on Dec. 17, 2014, entitled "Bone Marrow Aspirating Probe" and naming Brian W. Su et al. as inventors. The above-referenced patent application is hereby incorporated by reference herein in its entirety.

B. BACKGROUND

The invention relates generally to the field of harvesting bone marrow from bones, such as the human long bones, pelvis, and vertebral bodies.

Existing techniques for removing bone marrow typically involve the use of syringes or fenestrated instruments attached to a syringe. Such techniques may require repeated attempts to remove enough bone marrow to be effective as when used on carriers for bone graft substitutes, for example. In addition, fenestrated instruments can be prone to clogging and the sharp tip of a Jamshidi type needle can place vital structures such as nerves and blood vessels at risk during the extraction of the bone marrow. Furthermore, fenestrated instruments aspirate from a small select portion of the bone rather than along the entire length of the bone.

C. BRIEF DESCRIPTION OF THE DRAWINGS

Other objects and advantages of the invention may become apparent upon reading the detailed description and upon reference to the accompanying drawings.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

D. DETAILED DESCRIPTION

Figure 1:
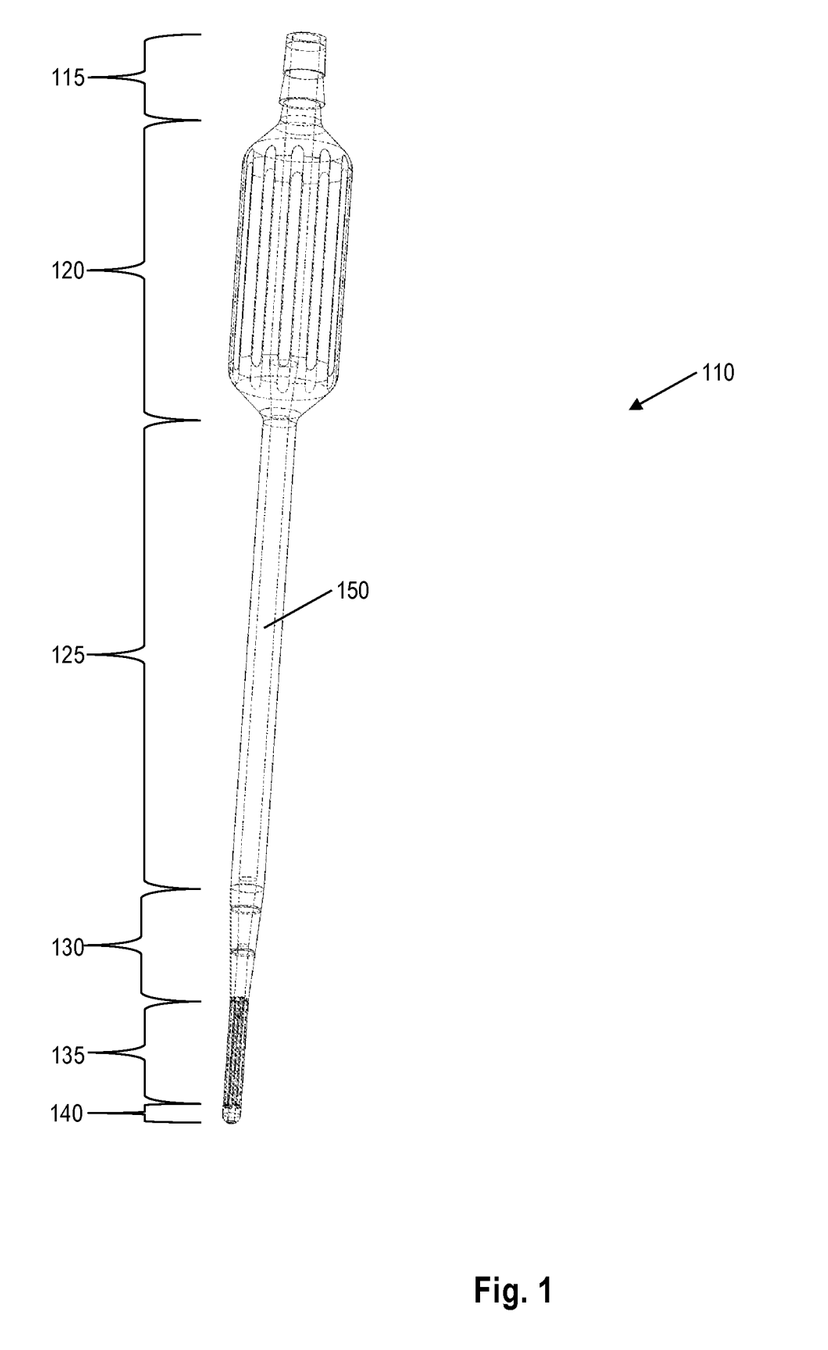
FIG. 1 is a diagram illustrating a probe for aspirating bone marrow, in accordance with some embodiments.

FIG. 1 is a diagram illustrating a probe for aspirating bone marrow, in accordance with some embodiments.

Aspirating probe 110 is configured to aspirate bone marrow from within bones. Aspirating probe 110 may be a disposable or a reusable aspirating probe configured to harvest bone marrow from various bones in a human or animal body.

In some embodiments, aspirating probe 110 may include several sections. It should be noted that in some alternative embodiments aspirating probe 110 may include additional sections from the ones shown or discussed here. In yet other alternative embodiments, some of the sections shown here may not be included or may be included in alternative orders.

Section 115 is a coupling section configured to couple aspirating probe 110 to a tube in order to transport extracted bone marrow from the probe. Accordingly, section 115 may be shaped in a way that allows the tube to more slip on to the probe relatively easily but does not permit easy removal of the tube from the probe. In addition, section 115 is configured to seal against the inside of the tube in order to prevent leakage of bone marrow. In some embodiments, the tube, on the other end, may be coupled to a suction device to facilitate the removal of bone marrow from the bone.

Section 120 is a handle section configured to be held within the fingers of a professional performing the bone marrow extraction procedure. In some embodiments, section 120 may be constructed with a diameter that is larger than the other parts of the probe in order to make it easier for a professional to handle the probe. Section 120 may also include ridges as well as other features that increase the friction between the probe and the fingers to make the probe easier to handle.

Section 125 is an extension section configured to add, as needed, additional length to the probe. For example, the probe may be designed to extend a certain amount above the patient's body, and the length of section 125 may be chosen accordingly. The length of the probe may also affect the handling of the probe by the administering professional; thus, the length of the probe may again be chosen accordingly. Section 125 also houses inner cavity/tube 150, which is configured to transport the extracted bone marrow through and out of the probe for collection. In some embodiments, inner cavity/tube 150 extends within sections 115, 120, 125, and 130 for transporting bone marrow within those sections.

Section 130 is a tapered portion of the probe and is configured to dock and form a seal against a hole that is drilled into the bone from which bone marrow is to be extracted.

In some embodiments, the bottom of section 130 may have a diameter that is slightly smaller than the diameter of the hole in the bone, and the top of section 130 may have a diameter that is slightly larger than the diameter of the hole. The diameter of section 130 may taper from the smaller diameter at the bottom to the larger diameter at the top. Accordingly, as aspiration probe 110 is being pushed into a hole in the bone, a stopping point is reached and a substantial seal is formed between the sides of the hole and the tapered section of the probe. Such a seal may facilitate, for example, a more efficient removal of the bone marrow as the seal may prevent the loss of suction. In some embodiments, the physician or other user/operator may perform the removal of the bone marrow by alternating between having the probe against the bone (forming a substantial seal) and having the probe away from the bone (breaking the seal) as well as optionally rotating the probe inside the bone to enhance the bone marrow removal.

In some embodiments, the probe tip may be tapered from 4 mm to 7.5 mm. Accordingly, the probe may be configured to dock with and seal against a hole having a diameter that is within that range (4 mm to 7.5 mm).

It should be noted that, in some embodiments, section 130 may not be have a taper. Section 130 may, for example, have a cross section diameter that has substantially the same value from the top to the bottom of the section. In some embodiments, the exterior diameter of the cross section of the section may be less than the diameter of the hole in the bone such that the section may fit through the hole.

Section 135 comprises flutes/longitudinal channels along which bone marrow may be "vacuumed" into the aspiration probe. In some embodiments, the aspiration probe may comprise openings for the evacuation of bone marrow that are placed to the sides of the probe. The non-fenestrated opening/openings on the side of the probe can be made larger and thus better accommodate the flow of bone marrow while avoiding clogging. In some embodiments, bone marrow is configured to flow along the flutes of section 135 and enter the probe into one or more openings at the bottom of section 130. In some embodiments, the one or more of the openings correspond to the one or more flutes/longitudinal channels.

In some embodiments, the length of section 135 may be chosen according to the "depth" of the bone from which the probe is designed to extract bone marrow. Accordingly, the length of the probe below the tapered section may be chosen such that the probe is positioned deep enough into the bone for better bone marrow extraction but not too deep as to puncture through or otherwise damage the inside of the other side of bone. In some embodiments, the length of section 135 may also be chosen as to optimize the suction of bone marrow from the bone.

It should be noted that, in some embodiments, section 135 and the flutes may be very small in length, extending a very small distance below the corresponding holes of section 130. In yet other embodiments, section 135 and the flutes may not be used at all, leaving only the hole(s) of section 130 for suction. In such embodiments, one or more holes may be used.

Section 140 is the tip of aspiration probe 140. In some embodiments, section/tip 140 is made blunt so as to not injure the bone, in case the tip comes into contact with the bone. In some embodiments, section 140 may be optional, as are other sections of the probe.

In some embodiments, an x-ray marker may be placed inside aspiration probe 110. In some embodiments, the x-ray marker may be placed at the lower end of aspiration probe 110. In some embodiments, the x-ray marker may extend along a large portion inside the middle of section 135 so as to make the x-ray marker more visible. The x-ray marker may aid a physician or other professional operator in determining the position of aspiration probe 110 inside a bone in which the probe has been inserted. The physician or other operator may take an x-ray, for example, after inserting the probe into the bone to determine whether the probe has been inserted to an appropriate depth. In some embodiments, aspiration probe 110 may be metallic. In other embodiments, any other material may be used for the x-ray marker such that enough contrast is provided between the probe and surrounding tissue during the x-ray.

In yet other embodiments, other imaging techniques may be used. Accordingly, the marker may be constructed using a material that would provide appropriate contrast between the marker and surrounding tissue for the type of medical imaging method being used.

In some embodiments, the aspiration probe may be used to extract bone marrow from a lumbar pedicle. Though the aspiration probe is shown in the examples shown here as being used with lumbar pedicles, it should be noted, that the probe may be used with other bones. The aspiration probe (in some embodiments, with appropriate modifications) may be used in the extraction of bone marrow from cervical, thoracic, or lumbar vertebral bones and with probe entry into the bones accessed anteriorly or laterally. The aspirating probe may also be adapted for use with the ilium (hip) or long bone (humerus or femur).

In some embodiments, the aspiration probe may be configured to "dock" to a specific bone structure with aspiration port features in order to retrieve bone marrow material from a specific region within the bone.

In some embodiments, the aspiration probe may be constructed from medical-grade plastic. Various other materials may also be used in constructing the probe.

Figure 2:
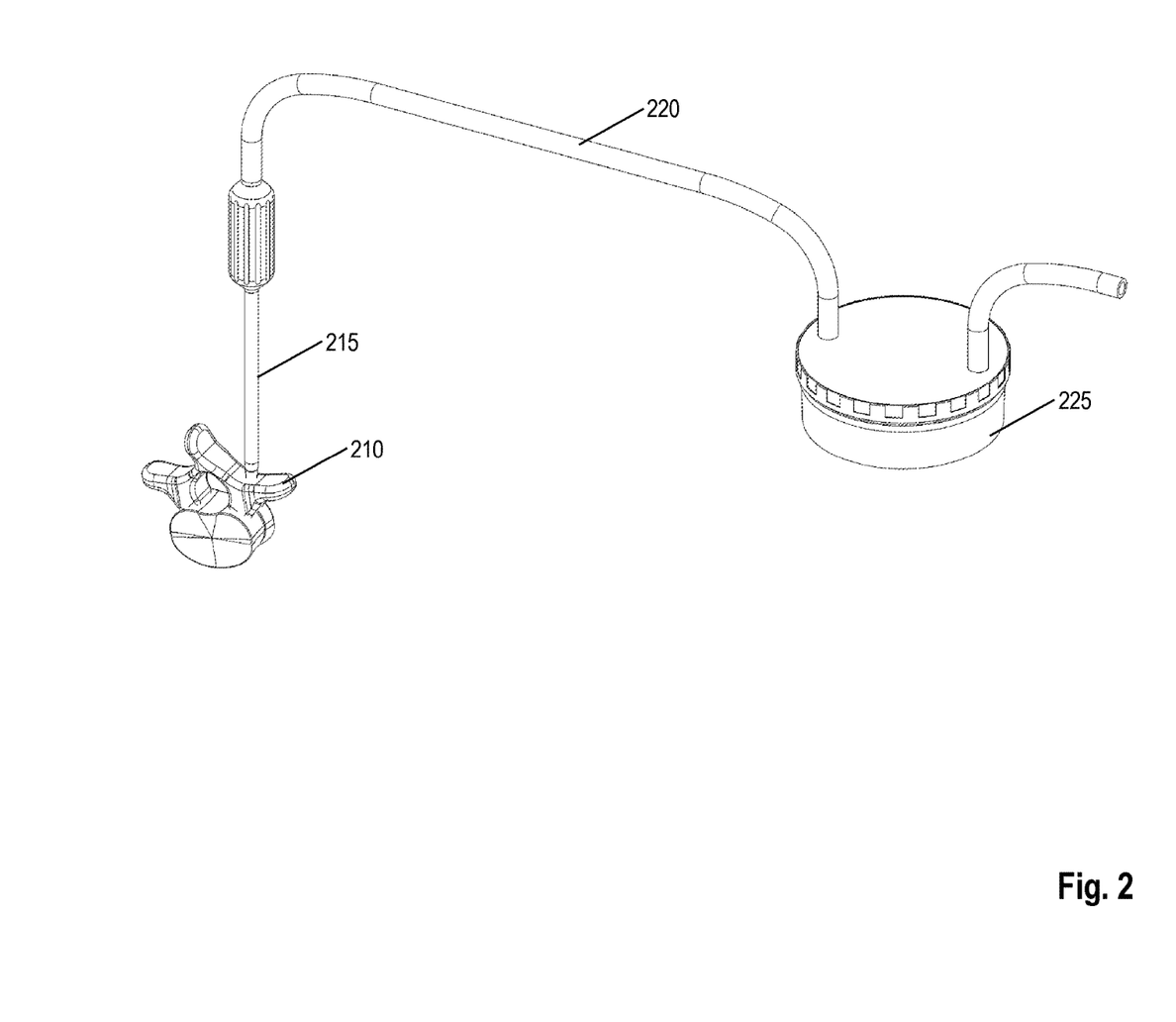
FIG. 2 is a diagram illustrating a system for aspirating bone marrow, including an aspiration probe, vacuum tubes, and a trap, in accordance with some embodiments.

FIG. 2 is a diagram illustrating a system for aspirating bone marrow, including an aspiration probe, vacuum tubes, and a trap, in accordance with some embodiments.

In some embodiments, the bone marrow aspiration system comprises aspiration probe 215, which is configured to dock into lumbar vertebral body 210 for the extraction of bone marrow. Aspiration probe 215 is coupled to trap 225 through tube 220, and trap 225 is connected to a vacuum pump (not shown here) through another tube.

In some embodiments, aspiration probe 215 is configured to dock into a port/hole drilled (or otherwise formed) into lumbar vertebral body 210. In some embodiments, a substantial seal may be formed between aspiration probe 215 and lumbar vertebral body 210 to aid the suction of the bone marrow. As the bone marrow is being vacuumed through tube 220, the bone marrow may be trapped in trap 225.

Figure 3:
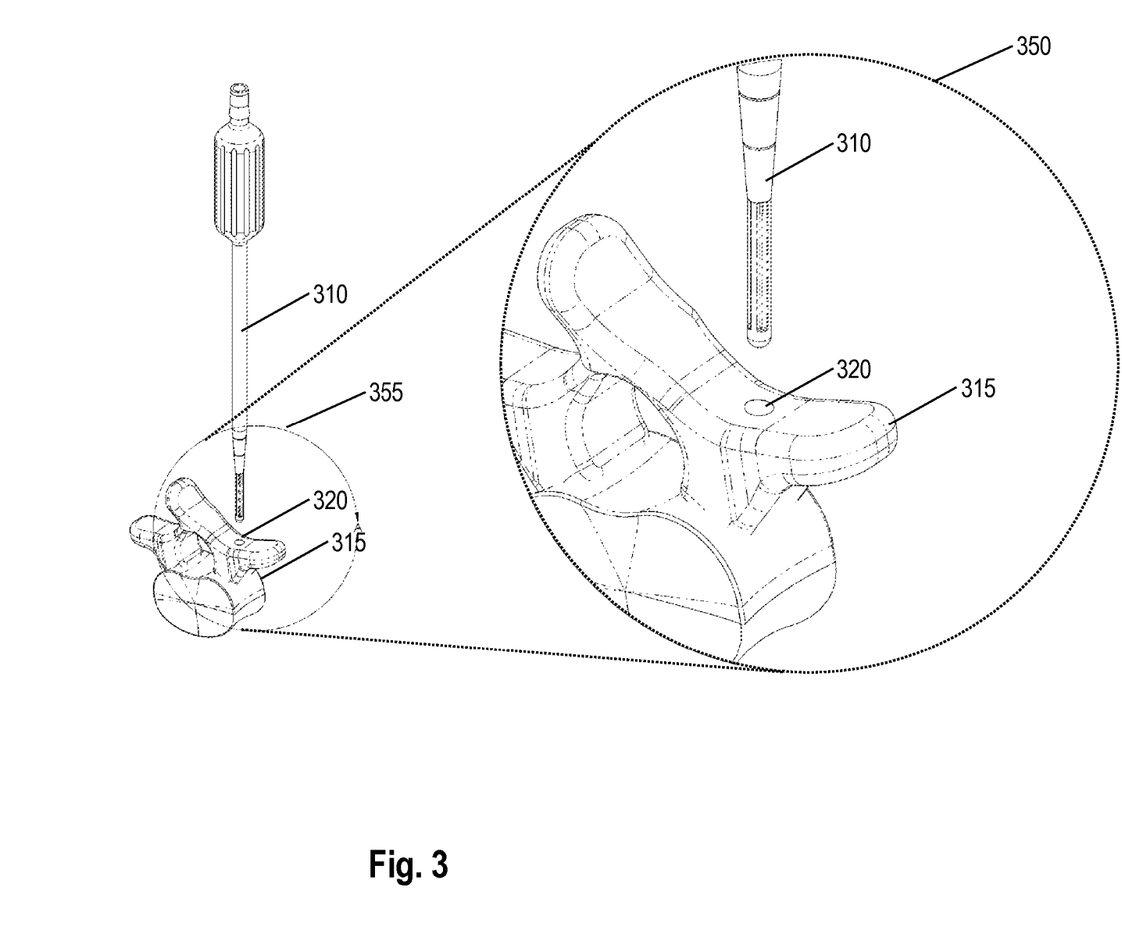
FIG. 3 is a diagram illustrating an aspiration probe being inserted into a pedicle, in accordance with some embodiments.

FIG. 3 is a diagram illustrating an aspiration probe being inserted into a pedicle, in accordance with some embodiments.

In the figure, view 350 is an expanded view of view 355. Aspiration probe 310 is shown as the aspiration probe is about to be inserted (or removed) from vertebral body 315. Aspiration probe 310 is configured to be inserted into vertebral body 315 through hole 320.

In some embodiments, various instruments and methods may be used to establish and verify the dimensions of a "hole" in a bone into which the aspiration probe may dock. In some embodiments, the hole may be established with specific properties, such as a specific width, a specific depth, a specific profile (such as shape, curvature, etc.), etc.

Instruments such as an awl and a "gear shift" are some examples of tools that may be used to establish the hole. One of those or another tool may be used to verify the distance to the other side of the bone. In alternative embodiments, other tools may be used to establish the hole, such as a variety of medical drills.

Figure 4:
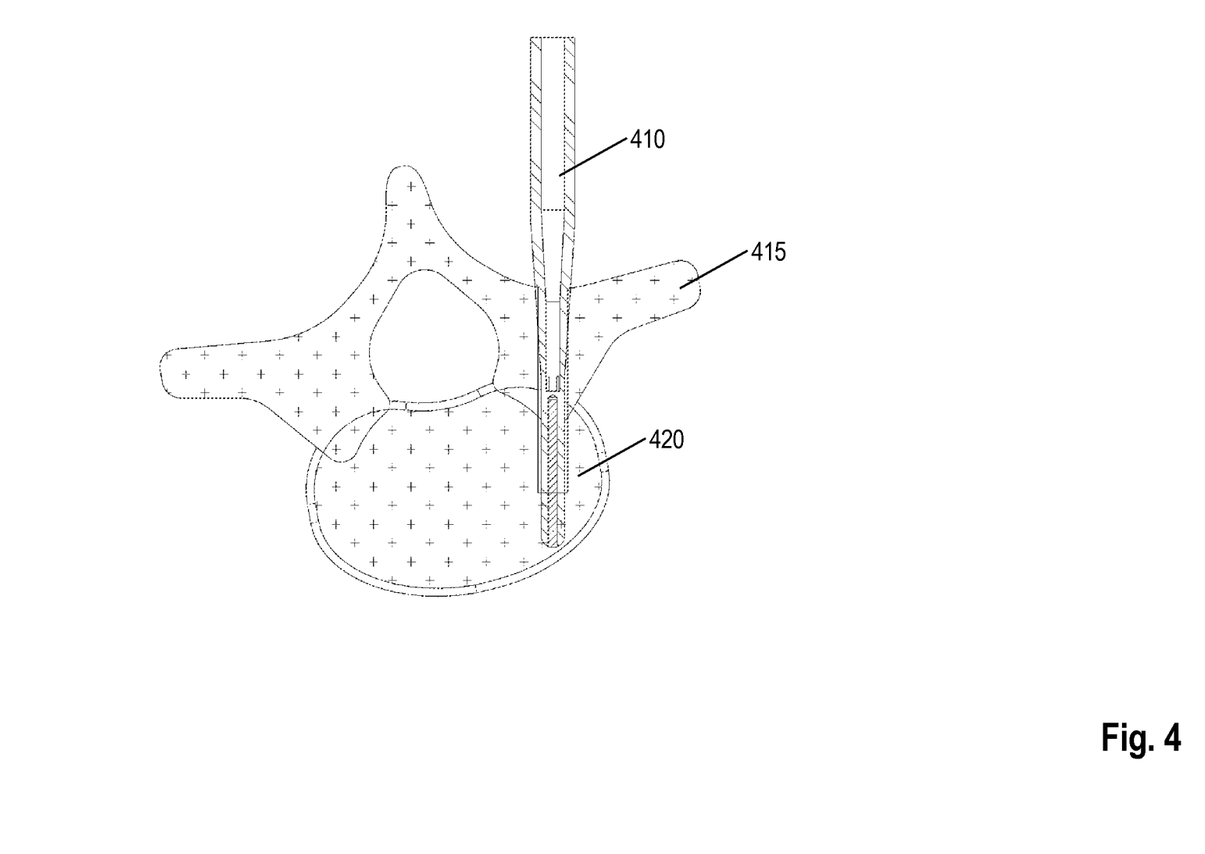
FIG. 4 is a diagram illustrating an aspiration probe inside a pedicle for extracting bone marrow, in accordance with some embodiments.

FIG. 4 is a diagram illustrating an aspiration probe inside a pedicle for extracting bone marrow, in accordance with some embodiments.

Aspirating probe 410 is shown here inserted into vertebral body 415 for the purpose of extracting bone marrow 420 from within the vertebral body. In some embodiments, the tapered section of the probe is configured in such a position as to ensure that the probe does penetrate beyond the limits of the cavity. In addition, the blunt/soft tip at the end of the probe is configured so as not to cause damage to the inside of the bone cavity in the event that the tip touches the inside of the bone cavity.

Figure 5:
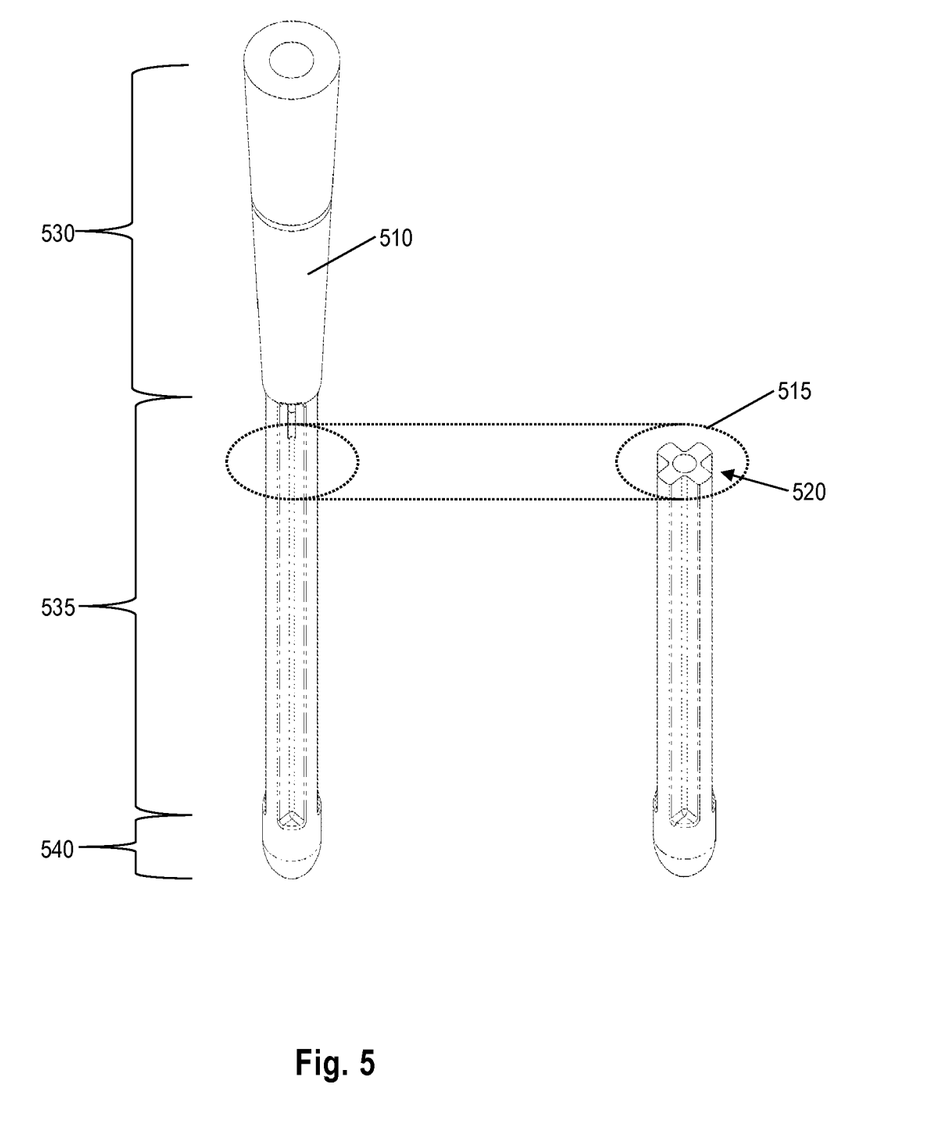
FIG. 5 is a diagram illustrating a cross sectional area of a portion of an aspiration probe, in accordance with some embodiments.

FIG. 5 is a diagram illustrating a cross sectional area of a portion of an aspiration probe, in accordance with some embodiments.

The lower three sections of aspiration probe 510 are shown here, in accordance with some embodiments: tapered section 530, flute section 535, and tip section 540.

In some embodiments, the longitudinal channels for the suction and removal of bone marrow may be placed on the sides of the aspiration probe in section 535. In some embodiments, the suction openings may be designed to resemble a crucifix in cross section, as may be seen by cross-section 515. Other designs may also be used, however. In addition, a smaller number or a larger number than four channels may be used.

In some embodiments, section 535 may include four flutes or channels that may be defined by crucifix 550. In some embodiments, tapered section 530 may include at the bottom four openings that correspond to the four flutes of flute section 535. Accordingly, during suction, bone marrow may travel along the flutes and enter the probe through the openings at the bottom of tapered section 530. The suction, in some embodiments, may be caused by a pump, to which aspiration probe 510 is coupled.

In some embodiments, placing the channels on the sides of the probe, facilitates the usage of larger openings for the suction of bone marrow, reducing the probability of clogging the probe. In some embodiments, the flutes may be used with the corresponding openings above the flutes to facilitate the channeling of bone marrow from the lower portions of the flutes up and into the openings for suction/removal.

In some embodiments, the aspiration probe may include a blunt tip as may be seen in section 540, reducing the risk of damage to vessels, nerves, or bone from the probe during the insertion and extraction of the bone marrow.

In some embodiments, section 530 above the flutes of the aspiration probe may be tapered in order to facilitate the formation of a seal between the probe and the bone when the probe is docked into the bone, enhancing the suction/removal of bone marrow.

Figure 6:
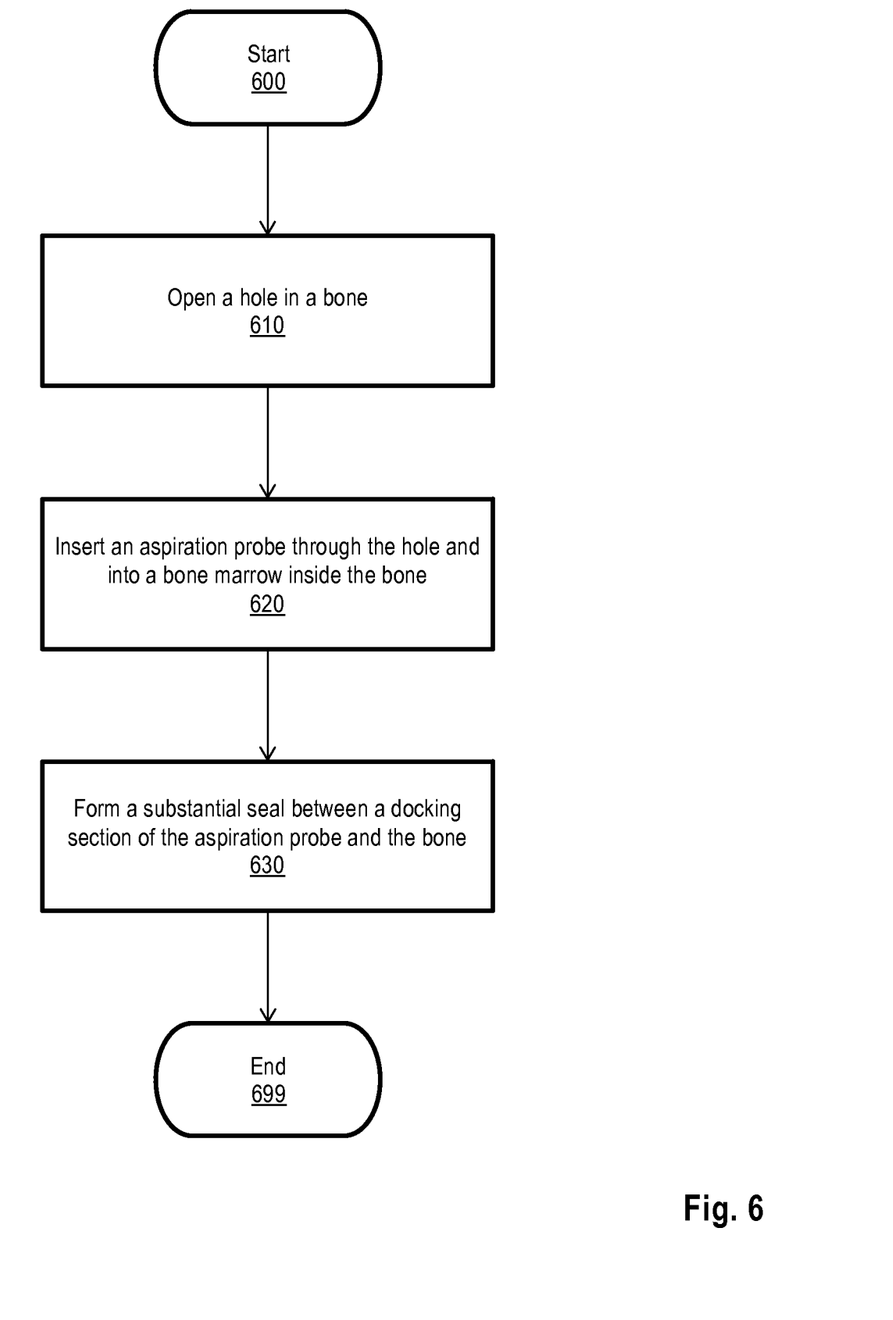
FIG. 6 is a flow diagram illustrating a method for extracting bone marrow, in accordance with some embodiments.

FIG. 6 is a flow diagram illustrating a method for extracting bone marrow, in accordance with some embodiments.

In some embodiments, the method described here may be implemented at least partially by using the devices shown in FIG. 1 through FIG. 5.

Processing begins at 600 where, at block 610, a hole is opened is opened in a bone from which bone marrow is to be extracted. In some embodiments, various instruments may be used to establish the hole, such as a medical bone drill.

At block 620, an aspiration probe is inserted through the hole and into the bone marrow. In some embodiments, at least a portion of the suction part of the probe is inserted into the probe.

At block 630, a substantial seal is formed between a docking section of the aspiration probe and the bone. In some embodiments, the docking section has a tapered portion to facilitate the formation of a substantial seal between the aspiration probe and the Processing subsequently ends at 699.

Figure 7:
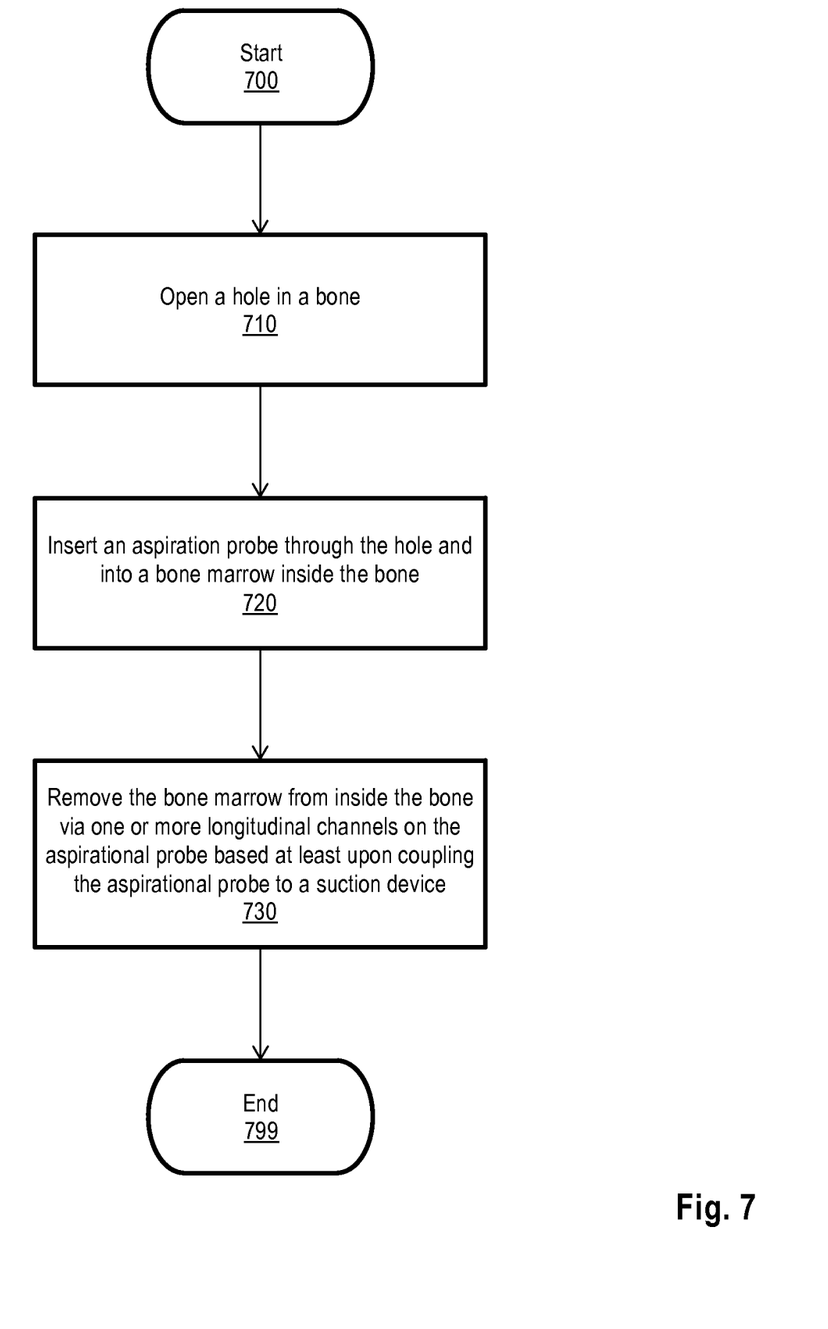
FIG. 7 is a flow diagram illustrating a method for extracting bone marrow, in accordance with some embodiments.

FIG. 7 is a flow diagram illustrating a method for extracting bone marrow, in accordance with some embodiments.

In some embodiments, the method described here may be implemented at least partially by using the devices shown in FIG. 1 through FIG. 5.

Processing begins at 700 where, at block 710, a hole is opened is opened in a bone from which bone marrow is to be extracted. In some embodiments, various instruments may be used to establish the hole, such as a medical bone drill.

At block 720, an aspiration probe is inserted through the hole and into the bone marrow.

At block 730, the bone marrow is removed from inside the bone via one or more longitudinal channels on the aspirational probe based at least upon coupling the aspirational probe to a suction device.

Processing subsequently ends at 799.

One or more embodiments of the invention are described above. It should be noted that these and any other embodiments are exemplary and are intended to be illustrative of the invention rather than limiting. While the invention is widely applicable to various types of systems, a skilled person will recognize that it is impossible to include all of the possible embodiments and contexts of the invention in this disclosure. Upon reading this disclosure, many alternative embodiments of the present invention will be apparent to persons of ordinary skill in the art.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations that follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. An aspiration probe, the aspiration probe comprising:
    a tip section;
    a fluted section, wherein a distal end of the fluted section is coupled to a proximal end of the tip section, wherein the fluted section comprises two or more longitudinal channels; and
    a docking section, wherein a distal end of the docking section is coupled to a proximal end of the fluted section,
    wherein the docking section comprises a docking inner cavity configured to transport bone marrow,
    wherein the docking section comprises two or more openings into the docking inner cavity, wherein the openings are positioned at the distal end of the docking section,
wherein the two or more openings correspond to the two or more longitudinal channels,
wherein the two or more longitudinal channels are configured to be placed within bone marrow through a hole in a bone,
wherein an outside surface of the docking section is tapered from a first diameter to a second diameter,
wherein the docking section is configured to be inserted partially into the hole in the bone,
wherein the outside surface of the docking section is configured to form a substantial seal against the hole in the bone based at least upon the diameter of the hole being smaller than the first diameter and larger than the second diameter,
wherein the two or more longitudinal channels extend longitudinally along the fluted section and along each of the other two or more longitudinal channels,
wherein the two or more longitudinal channels are recessed below an outer surface of the fluted section,
wherein the openings are configured to be coupled to a suction device for generating suction, and
wherein the one or more longitudinal channels are configured to channel the bone marrow from within the bone into the openings based at least upon the generating suction.

2. The aspiration probe of wherein an outside surface of the tip section is configured to contact an inner surface of the bone in a non-damaging manner based at least upon the tip section being pressed against the bone.

3. The aspiration probe of claim 2, further comprising an extension section, wherein a distal end of the extension section is coupled to a proximal end of the docking section, wherein the extension section comprises an extension inner cavity configured to transport bone marrow, wherein the extension inner cavity is coupled to the docking inner cavity.

4. The aspiration probe of claim 3, further comprising a handle section, wherein a distal end of the handle section is coupled to a proximal end of the extension section, wherein the handle section comprises a handle inner cavity configured to transport bone marrow, wherein the handle inner cavity is coupled to the extension inner cavity.

5. The aspiration probe of claim 4, further comprising a coupling section, wherein a distal end of the coupling section is coupled to a proximal end of the handle section, wherein the coupling section comprises a coupling inner cavity configured to transport bone marrow, wherein the coupling inner cavity is coupled to the handle inner cavity, wherein the coupling section is configured to couple through a tube to the suction device.

6. A method comprising:
forming a hole in a bone;
inserting an aspiration probe through the hole into a bone marrow inside the bone;
causing removal of the bone marrow from inside the bone via two or more longitudinal channels on sides of a fluted section of the aspiration probe based at least upon coupling the aspiration probe to a suction device; and
causing, based at least upon coupling the aspiration probe to the suction device, the bone marrow to flow from the fluted section into a docking section of the aspiration probe and through a docking inner cavity within the docking section, the bone marrow entering the docking section through two or more openings positioned at a distal end of the docking section,
wherein a distal end of the fluted section is coupled to a proximal end of a tip section,
wherein the distal end of the docking section is coupled to a proximal end of the fluted section,
wherein the two or more openings correspond to the two or more longitudinal channels,
wherein the two or more longitudinal channels extend longitudinally along the fluted section and along each of the other two or more longitudinal channels,
wherein the two or more longitudinal channels are recessed below an outer surface of the fluted section,
wherein the two or more openings correspond to the two or more longitudinal channels,
wherein an outside surface of the docking section is tapered from a first diameter to a second diameter,
wherein, based at least upon the inserting the aspiration probe through the hole into the bone, the outside surface of the docking section is configured to form a substantial seal against the hole in the bone based at least upon the diameter of the hole being smaller than the first diameter and larger than the second diameter.

7. The method of claim 6, wherein an outside surface of the tip section is configured to contact safely an inside of the bone based at least upon the tip section being pressed against the bone.

8. The method of claim 7, further comprising an extension section, wherein a distal end of the extension section is coupled to a proximal end of the docking section, wherein the extension section comprises an extension inner cavity configured to transport bone marrow, wherein the extension inner cavity is coupled to the docking inner cavity.

9. The method of claim 8, further comprising a handle section, wherein a distal end of the handle section is coupled to a proximal end of the extension section, wherein the handle section comprises a handle inner cavity configured to transport bone marrow, wherein the handle inner cavity is coupled to the extension inner cavity.

10. The method of claim 9, further comprising a coupling section, wherein a distal end of the coupling section is coupled to a proximal end of the handle section, wherein the coupling section comprises a coupling inner cavity configured to transport bone marrow, wherein the coupling inner cavity is coupled to the handle inner cavity, wherein the coupling section is configured to couple through a tube to the suction device.

\* \* \* \* \*